United States Patent [19]

Pickenhagen et al.

[11] 4,006,261
[45] Feb. 1, 1977

[54] FLAVORING WITH MIXTURES OF THEOBROMINE AND CYCLIC DIPEPTIDES

[75] Inventors: Wilhelm Pickenhagen, Onex; Paul Dietrich, Chene-Bourg, both of Switzerland; Borivoj Keil, St. Remy les Chevreuse; Edgar Lederer, Sceaux-Seine, both of France

[73] Assignee: Firmenich S.A., Geneva, Switzerland

[22] Filed: Mar. 24, 1976

[21] Appl. No.: 669,832

Related U.S. Application Data

[63] Continuation of Ser. No. 508,726, Sept. 24, 1974, abandoned.

[30] Foreign Application Priority Data

Sept. 28, 1973 Switzerland .................. 13957/73

[52] U.S. Cl. .................................................. 426/537
[51] Int. Cl.$^2$ ..................................... A23L 1/234
[58] Field of Search ........................... 426/533, 537

[56] References Cited

UNITED STATES PATENTS

| | | | |
|---|---|---|---|
| 2,816,834 | 12/1957 | Ruskin | 426/533 |
| 2,835,590 | 5/1958 | Rusoff | 426/533 |
| 2,835,592 | 5/1958 | Rusoff | 426/533 X |
| 2,835,593 | 5/1958 | Rusoff | 426/533 X |
| 2,887,384 | 5/1959 | Rusoff | 426/533 |
| 2,887,385 | 5/1959 | Rusoff | 426/533 |
| 2,887,386 | 5/1959 | Rusoff | 426/533 |
| 2,887,387 | 5/1959 | Rusoff | 426/533 |
| 2,887,388 | 5/1959 | Rusoff | 426/533 |

OTHER PUBLICATIONS

Matoba et al. "Relationship Between Bitterness of Peptides and their Chemical Structure," Agr. Biol. Chem. 36, 1423–1431 (1972).
Holms, "The Taste of Amino Acids Peptides and Proteins," J. Agr. Food Chem., 17, 686–688 (1969).
Menamura et al., "Bitter Peptides in Cows Milk Digests with Bacterial Proteinase," Agr. Biol. Chem., 36, 588–595 (1972).

*Primary Examiner*—Joseph M. Golian
*Attorney, Agent, or Firm*—Pennie & Edmonds

[57] ABSTRACT

Compositions useful in the flavoring of foodstuffs and the like to impart bitterness and astringent flavor thereto wherein said composition comprises compounds A and B, said A compound being a cyclic dipeptide and said B compound being a purine derivative.

6 Claims, No Drawings

FLAVORING WITH MIXTURES OF THEOBROMINE AND CYCLIC DIPEPTIDES

This is a continuation of application Ser. No. 508,726 filed Sept. 24, 1974, and now abandoned.

BACKGROUND OF THE INVENTION

Much attention has been devoted in the past to the reproduction of the gustative notes which typically define the bitter character of certain foodstuffs. In the flavour industry there is in fact a need to provide flavouring ingredients, or compositions thereof, for improving the flavours of beverages or solid foodstuffs, particularly those comprising cocoa or a cocoa imitating substitute, by imparting to said products the distinct bitterness which characterizes the natural cocoa products. Sofar, however, no satisfactory solution has been found to this problem.

The term "bitterness", as used in the course of the present description, is deemed to define the gustative property possessed by a given substance of developing a bitter taste.

Most of these substances find their origin in the vegetable kingdom and they often occur in a variety of plants, such as those belonging to the families of Gentianaceae, Compositae and labiates. Equally, some foodstuffs having a base of animal origin possess a bitter taste when subjected to certain treatments.

The properly so called "bitter substances" do not include however the alkaloid derivatives of purine, whose bitter taste is very often viewed as a side effect [K. Herrmann, Deutsche Lebensmittel Rundschau, 68, 105(1972)].

Most of the bitter substances known hitherto belong either to the class of terpenoids possessing a lactonic or ketonic functional group or to that of phenol derivatives, such as for instance the compounds of the flavanone series found in citrus fruits. Peptides possessing a bitter taste are also known and their organoleptic properties are described in several scientific publications, viz. Zeit. fur Lebensmittel-Untersuch. Forsch., 147, 64 (1971); idem, 149, 321 (1972); Agr. Biol. Chem., 34, 729 (1970); J. Food Sci., 35, 215 (1970).

Certain amino acids [see e.g.: Greenstein and Winitz, Chemistry of the Aminoacids, vol. I, J. Wiley (1961) p. 150] as well as certain oligopeptides [Annual Meeting of the Agr. Chem. Soc. Japan, 42 (1972)] develop bitter gustative notes.

In the course of the past fiew years, several theories have been advanced in order to better define the relationships which may exist between the chemical structure of a given substance and its developed bitterness [see: Nature, 223, 97–9(1969)]. However, it has to be clearly stated that in the present state of our knowledge, it is impossible to predict the organoleptic properties of a compound on the sole base of its chemical structure. Not surprisingly therefore one may observe that the discovery of new flavouring ingredients, in particular of bitter flavouring ingredients, occurs very often in a pure accidental way.

THE INVENTION

The present invention provides a flavouring composition which comprises as active ingredients compounds A and B, said A compound being a member of the group consisting of an aminoacid and an oligopeptide, or any mixture of oligopeptides, said B compound being a purine derivative of formula

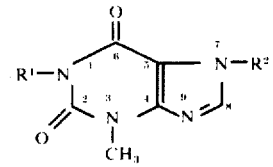

wherein each of symbols $R^1$ and $R^2$ represents a methyl radical or one of them represents a hydrogen atom and the other a methyl radical.

It has now been surprisingly discovered that by the use of the said flavouring composition of the invention, it was possible to modify, improve or enhance the organoleptic properties of foodstuffs, animal feeds, beverages, pharmaceutical preparations and tobacco products. More particularly, it has been found that by the use of the composition of the invention, it was possible to improve or confer a characteristic bitterness to the products to which it was added.

The present invention also relates to foodstuffs and beverages which comprise having added thereto a small but flavour modifying amount of said composition.

More particularly, the present invention relates to the aromatization of cocoa, cocoa products or cocoa imitating substitutes, and generally to improving their organoleptic properties.

A further object of the present invention is a process for enhancing, improving or modifying the taste and the flavour of cocoa, cocoa products or cocoa imitating substitutes, which process comprises added thereto a flavouring composition comprising as active ingredients compounds A and B, said A compound being a member of the group consisting of an aminoacid and an oligopeptide, or any mixture of oligopeptides, said B compound being a purine derivative of formula I.

By such a process of the invention, it is possible to correctly reproduce the gustative sensation, typically bitter and astringent, at one time, generated in the human perceptive system by the absorption of cocoa containing foodstuffs.

The cocoa flavour has been thoroughly studied in the past and several solutions have been suggested in order to reconstitute its natural aroma.

For instance, U.S. Pat. No. 2,835,590 describes the preparation of an artificial chocolate flavour by a process comprising treating a saccharide with an oligopeptide containing 2 to 6 aminoacid units. Bitterness and astringency were in this case conferred by the addition to the flavour composition of substances such as theobromine, caffeine, quinine or naringine, and tannins.

In the past, the bitter taste of cocoa was attributed to the presence therein of theobromine and caffeine; more particularly, it was believed that its bitterness was dependent on the relative proportions of the said purines [Handbuch der Lebensmittelchemie, vol. VI, Springer Verlag (1970) p. 232; Deutsche Lebensmittel-Rundschau, 68, 140 (1972)].

We have now discovered that the presence of one or the other of the said purines is a necessary, but insufficient condition for reconstituting the cocoa flavour. The presence of an aminoacid or an oligopeptide, or a mixture of oligopeptides, is equally essential. Suitable oligopeptides include di-, tri-, tetra-, penta- and hexapeptides. Dipeptides are however preferred. Among the variety of dipeptides which can be used as flavouring coingredients according to the invention, the following open chain and cyclic peptides are of particular interest:

| | | |
|---|---|---|
| Gly-Ala, | Gly-Val, | Gly-Leu, |
| Gly-Phe, | Gly-Pro, | Ala-Leu, |
| Ala-Val, | Ala-Phe, | Ala-Pro, |
| Val-Leu, | Val-Phe, | Val-Pro, |
| Leu-Phe, | Leu-Pro, | Phe-Pro, |
| Gly-Gly, | Ala-Ala, | Val-Val, |
| Leu-Leu, | Phe-Phe, | |
| as well as | | |
| (Cyclo)-Gly-Ala- | Ber., 39, 752 (1906) | |
| (Cyclo)-Gly-Val- | Ann., 363, 136 (1908) | |
| (Cyclo)-Gly-Leu- | Ber., 39, 2893 (1906) | |
| (Cyclo)-Gly-Phe- | Ann., 363, 1 (1908) | |
| (Cyclo)-Gly-Pro- | Ann., 363, 118 (1908) | |
| (Cyclo)-Ala-Leu- | Ber., 39, 2893 (1906) | |
| (Cyclo)-Ala-Val- | Ann., 363, 136 (1908) | |
| (Cyclo)-Ala-Phe- | W. Schoeller, Dissertation Berlin (1906) | |
| (Cyclo)-Ala-Pro- | Ber., 37, 2842 (1904) | |
| (Cyclo)-Val-Leu- | Ann., 363, 136 (1908) | |
| (Cyclo)-Val-Phe- | Z. phys. Chem., 214, 63 (1933) | |
| (Cyclo)-Val-Pro- | Hoppe-Seyler's Z. physiol.Chem., 132, 1 (1924) | |
| (Cyclo)-Leu-Phe- | Coll. Czech. Chem. Comm., 32, 3780 (1967) | |
| (Cyclo)-Leu-Pro- | Ann., 363, 118 (1908) | |
| (Cyclo)-Phe-Pro- | J. Biol. Chem., 155, 535 (1944) | |
| (Cyclo)-Pro-Asn- | n.c. | |
| (Cyclo)-Asn-Phe- | Hoppe-Seyler's Z. physiol. Chem., 174, 76 (1928) | |
| (Cyclo)-Gly-Gly- | J. Prakt. Chemie, 26, 175 (1887) | |
| (Cyclo)-Ala-Ala- | Ann., 134, 372 (1865) | |
| (Cyclo)-Val-Val- | Ann., 363, 136 (1908) | |
| (Cyclo)-Leu-Leu- | Ann., 69, 16 (1849) | |
| (Cyclo)-Phe-Phe- | Ann., 219, 179 (1883) | |

The conventional abbreviation for amino acids as used throughout the present application are "Gly" for glycine; "Ala" for alanine; "Val" for valine; "Leu" for leucine; "Ileu" for isoleocine; "Cys" for systeine; "Met" for Methionine; "Phe" for phenylalanine; "Pro" for proline, "Ser" for serine; "Thr" for threonine; "Tyr" for tyrosine; "Try" for tryptophan; "Asp" for aspacrtic acid; "Glu" for glutamic acid; "Arg" for arginine; "Lys" for lysine; and "His" for histidine. Further, in the course of the present description the cyclic dipeptides, also known under the name of diketopiperazines, are designated by the current abbreviation preceded by the term "Cyclo". For example, the term "Ala-Ala" designates alanyl-alanine, a compound of formula

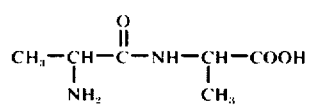

also defined as H-Ala-Ala-OH, whereas the term "(Cyclo)-Ala-Ala-" designates cyclo)ananyl-alanyl or 2,5-dimethyl-3,6-diketopiperazine, a compound of formula

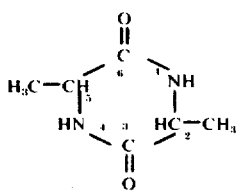

In the hereinabove list of compounds, immediately following the chemical name of each member, there is indicated the literature reference giving a method for its preparation. Some of the said compounds are commercially available and one of them is new and identified by the abbreviation n.c. Its preparation as well as that of the known compounds, can be achieved by the synthesis illustrated by the following reaction scheme:

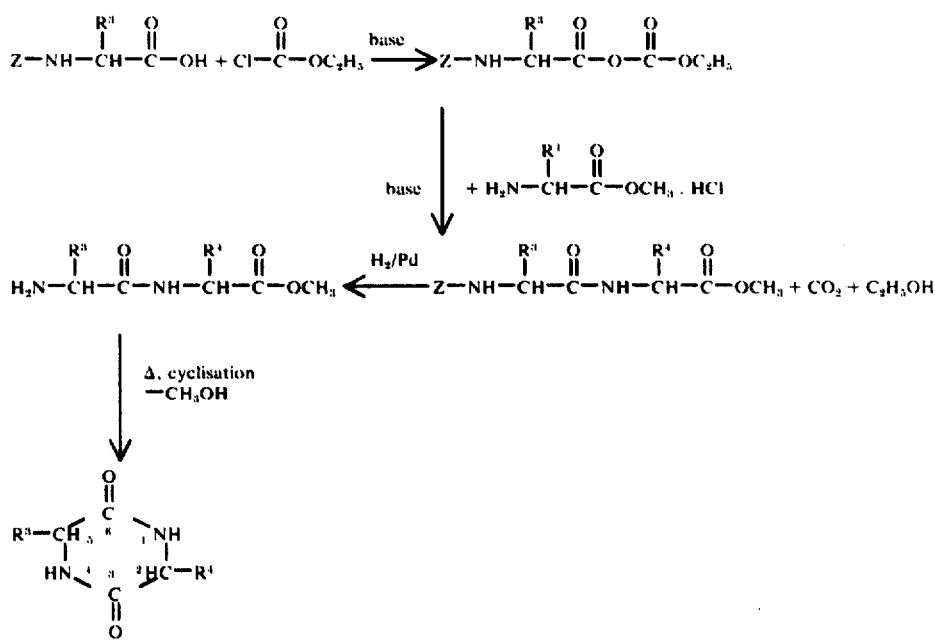

In the above given scheme, symbol Z represents a carbobenzoxylic radical of formula

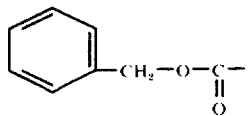

and R³ and R⁴ designate the characteristic substituents present in the molecule of the particular aminoacid employed as starting material. Thus, each of symbols R³ and R⁴ can, for instance, represent a hydrogen atom or an alkyl radical such as methyl, ethyl, propyl, isopentyl, 2-methyl-butyl or 2-phenyl-ethyl.

To exemplify the preparation of the dipeptides of the invention, we indicate hereinbelow the method followed [see also: Helv. Chim. Acta. 34, 874 (1951) and J. Org. Chem., 33, 864 (1968)].

5 mM of the N-carbobenzoxylic derivative of the chosen aminoacid were dissolved in a solution of 7.5 mM of N-methyl-morpholine in 20 ml of anhydrous tetrahydrofuran. The solution thus obtained was cooled to about −10° C and at this temperature 5.2 mM of ethyl chlorocarbonate were added thereto; then, the reaction mixture was left under stirring for 15 minutes.

A suspension of 5 mM of the methyl ester of the aminoacid hydrochloride chosen for the coupling and 7.5 mM of N-methyl-morpholine in 10 ml of dimethylformamide was added to the said mixture whose temperature was slowly increased up to about 20°–25° C while stirring. By filtration and evaporation of the volatile portions under vacuum (bath temperature of about 60° C), there was obtained a residue, which was then dissolved in about 500 ml of ethyl acetate. The resulting clear solution was washed twice with 10 ml of a 10% aqueous citric acid solution, then with 15 ml of a 7% solution of sodium bicarbonate and finally with 3 portions of brine. After drying over Na₂SO₄ and evaporation, the methyl ester of the N-carbobenzoxylic dipeptide was obtained as residue. This compound can be converted into its open chain or cyclic dipeptide according to one of the following methods:

A. PREPARATION OF AN OPEN CHAIN DIPEPTIDE

The methyl ester of the N-carbobenzoxylic dipeptide, prepared as indicated above, was saponified according to the method of Wieland et al. [Lieb.Ann. 1973, 45] by dissolving the raw product in 80 ml of dioxane and 6 ml of 1N NaOH and keeping then the resulting clear solution at room temperature under stirring for 1 hour.

The volatile portions were evaporated under reduced pressure at 20° C and the obtained residue was dissolved in 100 ml of water and washed twice with two portions of 50 ml each of ethyl acetate.

The aqueous phase was acidified with 2N HCl to pH 1 and extracted then with 4 fractions of 100 ml each of ethyl acetate. After the usual treatments of drying over Na₂SO₄ and evaporation, there was obtained a residue which was then subjected to a catalytic hydrogenation in the presence of palladium on charcoal.

B. PREPARATION OF CYCLIC DIPEPTIDES

The methyl ester of the N-carbobenzoxylic dipeptide, prepared as indicated above, was dissolved in 150 ml of methanol and subjected to a catalytic hydrogenation in the presence of palladium on charcoal. Ten minutes were generally sufficient for achieving a complete conversion; the solution, however, was kept under hydrogen atmosphere during 3 hours.

After filtration, an evaporation of the clear filtrate gave a residue mainly comprising the methyl ester of the open chain dipeptide which could then be cyclised according to the method of Nitecki et al., J. Org. Chem., 33, 864 (1968) by heating it in about 200 ml of a 96:4 mixture of toluene and sec.-butanol during 3 hours.

The cyclic dipeptide, obtained by evaporation of the volatile portions, was crystallized in methanol.

(Cyclo)-Pro-Asn-, which is a new compound, exhibits the following physical data:

m.p. 200°–202° C; $[\alpha]_D^{20}(H_2O) = -84.8°$ C
NMR (DMSO): 1.78 (4H,m); 2.40 (2H,m); 3.70–4.40 (4H,m); 6.75 (1H, broad s); 7.28 (1H, broad s); 7.80 (1H,s) δ ppm.

The compound can be represented by the following structural formula

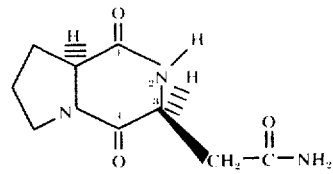

(3S-acetamido-1,4-dioxo-9S-2,5-pyrrolopiperazine or (Cyclo)-L-Pro-L-Asn).

A diastereoisomer of the said dipeptide had the following physical characteristics:

m.p. 249°–250° C; $[\alpha]_D^{20}(H_2O) = -61.7°$ C
NMR (DMSO): 1.75 (4H,m); 2.38 (3H,m); 3.65–4.20 (3H,m); 7.30 (1H, broad s); 7.92 (1H,d,J = 4 cps) δ ppm.

The following symmetrical cyclic dipeptides were prepared in accordance with the procedure described by E. Fischer [see: Ber., 39, 453 (1906)]:

(Cyclo)-Gly-Gly-, (Cyclo)-Ala-Ala, (Cyclo)-Val-Val-, (Cyclo)-Leu-Leu-, (Cyclo)-Phe-Phe-.

Thus, the methyl esters of the chosen aminoacids were heated at about 110° C for 3 hours. The reaction mixture solidified and the product was purified by crystallization in methanol.

PREFERRED EMBODIMENTS OF THE INVENTION

Among the variety of useful oligopeptides in accordance with the invention, cyclic dipeptides are preferred.

We have observed, moreover, that the most interesting flavouring effects were obtained by the use of compositions containing a mixture comprising at least two of the aforesaid cyclic dipeptides, the relative proportions of which can vary within a wide range.

According to a preferred embodiment of the invention, theobromine is used as preferred purine.

A particular object of the present invention is a flavouring composition comprising as active ingredient a cyclic dipeptide (diketopiperazine) in combination with theobromine.

A more particular object of the present invention is a flavouring composition comprising as active ingredient at least two cyclic dipeptides in combination with theobromine.

The proportions of the compositions of the invention to be used to achieve an interesting flavouring effect can vary within wide limits. For instance, proportions of the order of 5–10 ppm by weight based on the total weight of the flavoured materials to which they are added, can already produce perceptible effects.

Preferably, however, these proportions are from about 50 to 500 ppm. Higher proportions can be used whenever special effects are desired.

When the compositions of the invention are used to create novel flavouring compositions, these proportions can be as high as about 15%, or even more, but preferentially up to 1% of the weight of the composition. The ratio between the respective proportions of each flavouring ingredient in the compositions of the invention can equally vary within wide limits. Whenever a composition is constituted by a mixture comprising a single cyclic dipeptide and theobromine, the respective proportions of each ingredient are between 1.1:1 to 1:2. Whenever a composition is constituted by a mixture comprising two dipeptides and theobromine, particularly suitable weight ratios of the respective proportions of each ingredient are of between about 1:1:1 and 1:3:5. For example, the following standard compositions were prepared by mixing together the given ingredients in the proportions indicated as parts by weight:

| 1. | | |
|---|---|---|
| | (Cyclo)-Phe-Phe- | 10 |
| | (Cyclo)-Phe-Val- | 20 |
| | Theobromine | 100 |
| 2. | | |
| | (Cyclo)-Phe-Gly- | 30 |
| | (Cyclo)-Ala-Val- | 30 |
| | Theobromine | 100 |

Owing to the presence of one or more asymmetrical carbon atoms in their molecule, the aminoacids or the polypeptides of the invention can occur in the form of different configurational isomers. Thus, for instance the term "Ala-Phe" or "(Cyclo)-Ala-Phe-" designates one of the following isomeric peptides:

| D-Ala-L-Phe | and | (Cyclo)-D-Ala-L-Phe- |
|---|---|---|
| D-Ala-D-Phe | | (Cyclo)-D-Ala-D-Phe- |
| L-Ala-D-Phe | | (Cyclo)-L-Ala-D-Phe- |
| L-Ala-L-Phe | | (Cyclo)-L-Ala-L-Phe-, |
| respectively. | | |

Owing to the similarity of their organoleptic characters, each of the said isomers can be replaced by one of the others, or even mixtures thereof, without noticeably affecting the achieved flavour.

The preparation of the different configurational isomers of cyclic dipeptides is effected in accordance with the same procedure as that given above — see reaction scheme —. For example, the preparation of the four isomers of (Cyclo)-Ala-Phe- was carried out by coupling equimolecular amounts of the N-carbobenzoxylic derivative of L-alanine and the racemic methyl ester of phenylalanine hydrochloride on one hand, and the N-carbobenzoxylic derivative of D-alanine and the racemic methyl ester of phenylalanine hydrochloride on the other hand. Two pairs of diastereoisomers were thus obtained which, upon separation by means of column chromatography on silica gel, gave the four compounds in their pure isomeric form.

The following table summarizes the different isomeric forms of two members of the above mentioned class of cyclic dipeptides, viz. (Cyclo)-Ala-Phe- and (Cyclo)-Ala-Val-. Together with their analytical data, mention has been made of the nature of the starting materials used for their preparation.

| | Starting material | | m.p. | $\alpha_D$ | Analysis | | | | | | |
|---|---|---|---|---|---|---|---|---|---|---|---|
| | | | | | calculated | | | found | | | |
| Cyclic dipeptide | $NH_2$ side | COOH side | (° C) | $H_2O$ | %C | %H | %N | %C | %H | %N | Lit. |
| (Cyclo)-L-Ala-L-Phe- | Z-L-Ala- | PheOMe | 266–267 | +31.5° | 66.05 | 6.42 | 12.84 | 65.90 | 6.51 | 12.84 | (1) |
| (Cyclo)-D-Ala-D-Phe- | Z-D-Ala- | PheOMe | 266–268 | −60.0° | 66.05 | 6.42 | 12.84 | 65.90 | 6.59 | 12.82 | |
| (Cyclo)-D-Ala-L-Phe- | Z-D-Ala- | PheOMe | 253–256 | +80.1° | 66.05 | 6.42 | 12.84 | 65.91 | 6.53 | 12.87 | |
| (Cyclo)-L-Ala-D-Phe- | Z-L-Ala- | PheOMe | 253–255 | −80.0° | 66.05 | 6.42 | 12.84 | 65.97 | 6.59 | 12.99 | |
| (Cyclo)-L-Ala-L-Val- | Z-L-Ala- | ValOMe | 263–265 | −54.7° | 56.49 | 8.24 | 16.47 | 56.20 | 8.28 | 16.38 | (2) |
| (Cyclo)-D-Ala-D-Val- | Z-D-Ala- | ValOMe | 268–270 | +48.9° | 56.49 | 8.24 | 16.47 | 56.31 | 8.30 | 16.54 | |
| (Cyclo)-L-Ala-D-Val- | Z-L-Ala- | ValOMe | 273–276 | −26.7° | 56.49 | 8.24 | 16.47 | 55.63 | 8.26 | 16.32 | |
| (Cyclo)-D-Ala-L-Val- | Z-D-Ala- | ValOMe | 272–275 | +38.6° | 56.49 | 8.24 | 16.47 | 56.01 | 8.20 | 16.46 | |

Z = N-carbobenzoxylic radical
(1) W. Scholler, Doctorate Thesis, Univ. Berlin (1906)
(2) E. Fischer and H. Scheibler, Ann. Chem. 363, 136 (1908)

The invention is better illustrated but not limited by the following examples.

EXAMPLES

A.

A flavouring composition was prepared by mixing together during 1 hour under vigourous stirring the hereinbelow given oligopeptides and theobromine in 100 ml of commercial cow milk.

To the obtained solution, there were added 0.08 ml of a 10% alcoholic solution (95% ethanol) of commercially available cocoa flavour composition without bitter taste (Firmenich SA, Geneva, Switzerland, No. 51490) and 2g of soluble cocoa powder having a bland taste.

The taste of the beverage thus obtained was evaluated by comparison with a beverage prepared by dissolving 4g of soluble cocoa powder in 100 ml of milk.

The flavour experts have unanimously stated that the beverage flavoured with the flavouring composition above described presented a natural cocoa flavour, particularly with respect to its bitter and astringent character. Its aroma was in fact to a great extent similar to that developed by the beverage prepared with soluble cocoa alone.

B.

A second procedure of degustation consisted in evaluating the hereinbelow given compositions in mineral water (type: Evian) by comparison with solutions prepared by dissolving 2g of soluble cocoa powder in 50 ml of mineral water. The proportions used were the following:

3 mg of oligopeptide
6 mg of theobromine
30 ml of mineral water

In the following table the different tasted compositions are classified according to a relative scale of values, viz. "strongly bitter", "bitter" and "slightly bitter".

| Example | Composition | Evaluation |
|---|---|---|
| 1 | 1 mg (Cyclo)-Phe-Phe-<br>2 mg (Cyclo)-Phe-Val-<br>10 mg theobromine | strongly bitter |
| 2 | 1.5 mg (Cyclo)-Phe-Phe-<br>3 mg (Cyclo)-Ala-Val-<br>10 mg theobromine | strongly bitter |
| 3 | 3 mg (Cyclo)-Phe-Gly<br>3 mg (Cyclo)-Ala-Val-<br>10 mg theobromine | strongly bitter |
| 4 | 3 mg (Cyclo)-Pro-Ala-<br>3 mg (Cyclo)-Gly-Gly-<br>10 mg theobromine | bitter |
| 5 | 3 mg (Cyclo)-Ala-Gly-<br>3 mg (Cyclo)-Leu-Leu-<br>10 mg theobromine | bitter |
| 6 | 3 mg (Cyclo)-Phe-Pro-<br>3 mg (Cyclo)-Gly-Gly-<br>10 mg theobromine | slightly bitter |
| 7 | 3 mg (Cyclo)-Phe-Pro-<br>3 mg (Cyclo)-Leu-Leu-<br>10 mg theobromine | bitter |
| 8 | 3 mg (Cyclo)-Leu-Gly-<br>3 mg (Cyclo)-Pro-Asp-<br>10 mg theobromine | bitter |
| 9 | 3 mg (Cyclo)-Val-Gly-<br>3 mg (Cyclo)-Phe-Leu-<br>10 mg theobromine | slightly bitter |
| 10 | 3 mg (Cyclo)-Ala-Pro-<br>3 mg (Cyclo)-Phe-Val-<br>10 mg theobromine | strongly bitter |
| 11 | 5.5 mg (Cyclo)-Phe-Val-<br>10 mg theobromine | strongly bitter |
| 12 | 5.5 mg (Cyclo)-Leu-Gly-<br>10 mg theobromine | slightly bitter |
| 13 | 11 mg Val-Phe-<br>10 mg theobromine | slightly bitter |
| 14 | 3 mg (Cyclo)-Phe-Gly-<br>6 mg theobromine | bitter |
| 15 | 3 mg (Cyclo)-Phe-Ala-<br>6 mg theobromine | strongly bitter |
| 16 | 3 mg (Cyclo)-Phe-Leu-<br>6 mg theobromine | strongly bitter |
| 17 | 3 mg (Cyclo)-Phe-Val-<br>6 mg theobromine | strongly bitter |
| 18 | 3 mg (Cyclo)-Phe-Pro-<br>6 mg theobromine | slightly bitter |
| 19 | 3 mg (Cyclo)-Phe-Phe-<br>6 mg theobromine | strongly bitter |
| 20 | 3 mg (Cyclo)-Leu-Leu-<br>6 mg theobromine | bitter |
| 21 | 3 mg (Cyclo)-Leu-Val-<br>6 mg theobromine | bitter |
| 22 | 3 mg (Cyclo)-Leu-Ala-<br>6 mg theobromine | bitter |
| 23 | 3 mg (Cyclo)-Leu-Pro-<br>6 mg theobromine | slightly bitter |
| 24 | 3 mg (Cyclo)-L-Val-L-Ala-<br>6 mg theobromine | bitter |
| 25 | 3 mg (Cyclo)-L-Val-L-Gly-<br>6 mg theobromine | slightly bitter |
| 26 | 3 mg (Cyclo)-L-Ala-L-Ala-<br>6 mg theobromine | slightly bitter |
| 27 | 3 mg (Cyclo)-L-Ala-L-Gly-<br>6 mg theobromine | slightly bitter |
| 28 | 3 mg (Cyclo)-L-Ala-L-Pro-<br>6 mg theobromine | slightly bitter |
| 29 | 3 mg (Cyclo)-L-Gly-L-Gly-<br>6 mg theobromine | slightly bitter |
| 30 | 3 mg (Cyclo)-L-Gly-L-Pro-<br>6 mg theobromine | slightly bitter |
| 31 | 3 mg (Cyclo)-L-Pro-L-Asn-<br>6 mg theobromine | bitter |
| 32 | 3 mg (Cyclo)-L-Pro-L-Asp-<br>6 mg theobromine | slightly bitter |
| 33 | 3 mg (Cyclo)-D-Phe-Val-<br>6 mg theobromine | strongly bitter |
| 34 | 3 mg (Cyclo)-Phe-D-Val-<br>6 mg theobromine | strongly bitter |
| 35 | 3 mg (Cyclo)-D-Phe-D-Val-<br>6 mg theobromine | strongly bitter |
| 36 | 3 mg (Cyclo)-D-Val-Ala-<br>6 mg theobromine | bitter |
| 37 | 3 mg (Cyclo)-Val-D-Ala-<br>6 mg theobromine | bitter |
| 38 | 3 mg (Cyclo)-D-Val-D-Ala-<br>6 mg theobromine | bitter |
| 39 | 3 mg (Cyclo)-Pro-D-Asn-<br>6 mg theobromine | bitter |
| 40 | 3 mg (Cyclo)-Asn-Phe-<br>6 mg theobromine | bitter |

We claim:

1. A flavoring composition capable of imparting and enhancing a bitter and astrigent flavor to a foodstuff or beverage selected from the group consisting essentially of cocoa, a cocoa product or a cocoa imitating substitute which composition comprises, as an active ingredient, components A and B, said component A being a cyclic dipeptide or mixtures of two cyclic dipeptides and said component B being theobromine in the following weight ratios:
   a. when component A is a single cyclic dipeptide, in the weight ratio of from 1.1:1 to 1:2;
   b. when the component A is a mixture of two cyclic dipeptides, in the weight ratio of from about 1:1:1 to 1:3:5.

2. A flavouring composition according to claim 1 wherein the cyclic dipeptide is a member selected from the group of (Cyclo)-Phe-Val-, (Cyclo)-Phe-Leu-, Cyclo-Phe-Ala-and (Cyclo)-Phe-Phe-.

3. A flavouring composition according to claim 1 wherein the mixture comprising two cyclic dipeptides is a member selected from the group consisting of

| a. | (Cyclo)-Phe-Phe-<br>(Cyclo)-Phe-Val- | |
|---|---|---|
| b. | (Cyclo)-Phe-Phe-<br>(Cyclo)-Ala-Val- | |
| c. | [(Cyclo)-Gly-Gly-]<br>(Cyclo)-Ala-Val- | (Cyclo)-Phe-Gly- |
| d. | (Cyclo)-Ala-Pro-<br>(Cyclo)-Phe-Val-. | |

4. A flavouring composition according to claim 1 wherein the cyclic dipeptide is (Cyclo)-Asn-Phe.

5. A member selected from the group consisting of a cocoa, cocoa product or cocoa imitating foodstuff or beverage having added thereto the flavoring composition of claims 1 in from 5 to 500 ppm by weight based on the weight of the foodstuff or beverage.

6. A product according to claim 5 which is a cocoa imitating foodstuff.

* * * * *